(12) United States Patent
Saito et al.

(10) Patent No.: US 10,617,359 B2
(45) Date of Patent: Apr. 14, 2020

(54) ELECTRONIC DEVICE, SYSTEM, AND BODY CONDITION ESTIMATION METHOD

(71) Applicant: Kabushiki Kaisha Toshiba, Minato-ku, Tokyo (JP)

(72) Inventors: Mami Saito, Fujisawa Kanagawa (JP); Takashi Sudo, Fuchu Tokyo (JP); Yasuhiro Kanishima, Suginami Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 16/280,717

(22) Filed: Feb. 20, 2019

(65) Prior Publication Data

US 2020/0015745 A1    Jan. 16, 2020

(30) Foreign Application Priority Data

Jul. 11, 2018    (JP) .................. 2018-131606

(51) Int. Cl.
*A61B 5/00*       (2006.01)
*A61B 5/145*      (2006.01)
*G06F 1/16*       (2006.01)
*A61B 5/04*       (2006.01)
*A61B 5/0205*     (2006.01)
*A61B 5/11*       (2006.01)
*A61B 5/01*       (2006.01)

(52) U.S. Cl.
CPC .......... *A61B 5/681* (2013.01); *A61B 5/14517* (2013.01); *G06F 1/163* (2013.01); *A61B 5/01* (2013.01); *A61B 5/02055* (2013.01); *A61B 5/04* (2013.01); *A61B 5/1118* (2013.01); *A61B 5/746* (2013.01); *A61B 2562/029* (2013.01); *A61B 2562/0271* (2013.01)

(58) Field of Classification Search
None
See application file for complete search history.

(56) References Cited

U.S. PATENT DOCUMENTS

| 4,525,074 A * | 6/1985 | Murakami | A61B 5/103 340/309.16 |
| 2014/0141937 A1* | 5/2014 | Kim | A61B 5/222 482/8 |

(Continued)

FOREIGN PATENT DOCUMENTS

| JP | 2012-210233 A | 11/2012 |
| JP | 2019-125254 A | 7/2019 |

*Primary Examiner* — Fekadeselassie Girma
(74) *Attorney, Agent, or Firm* — Knobbe, Martens, Olson & Bear, LLP

(57) ABSTRACT

According to one embodiment, an electronic device includes a biological information acquisition processor, a body condition estimation processor, and a motion change detector. The biological information acquisition processor acquires biological information of a living body including information about the living body. The body condition estimation processor estimates a body condition of the living body based on the biological information. The motion change detector detects a motion change of the living body based on the biological information. The body condition estimation processor corrects a reference value used during body condition estimation or changes a body condition estimation method based on the motion change of the living body.

12 Claims, 6 Drawing Sheets

Worker

(56) References Cited

U.S. PATENT DOCUMENTS

| | | | |
|---|---|---|---|
| 2014/0172132 A1* | 6/2014 | Ura | A61B 5/6823 700/90 |
| 2014/0188257 A1* | 7/2014 | Ura | G09B 19/0038 700/91 |
| 2014/0275831 A1* | 9/2014 | Osorio | A61B 5/1118 600/301 |
| 2015/0206413 A1* | 7/2015 | Warner | G06Q 50/22 340/573.1 |
| 2015/0351673 A1* | 12/2015 | Vanslyke | A61B 5/1495 600/301 |
| 2016/0029954 A1* | 2/2016 | Sato | A61B 5/681 702/141 |
| 2016/0030807 A1* | 2/2016 | Matsumoto | A61B 5/1118 600/595 |
| 2017/0332979 A1* | 11/2017 | Nagisetty | A61B 5/7282 |
| 2018/0249917 A1* | 9/2018 | Sasahara | A61B 5/1118 |
| 2018/0249948 A1* | 9/2018 | Grabow | G06F 19/3481 |
| 2018/0374026 A1* | 12/2018 | Osawa | G06F 3/011 |
| 2019/0021617 A1* | 1/2019 | Uemura | H01L 31/042 |
| 2019/0021661 A1* | 1/2019 | Hasei | G06F 1/1635 |
| 2019/0021662 A1* | 1/2019 | Hiraide | A61B 5/742 |

\* cited by examiner

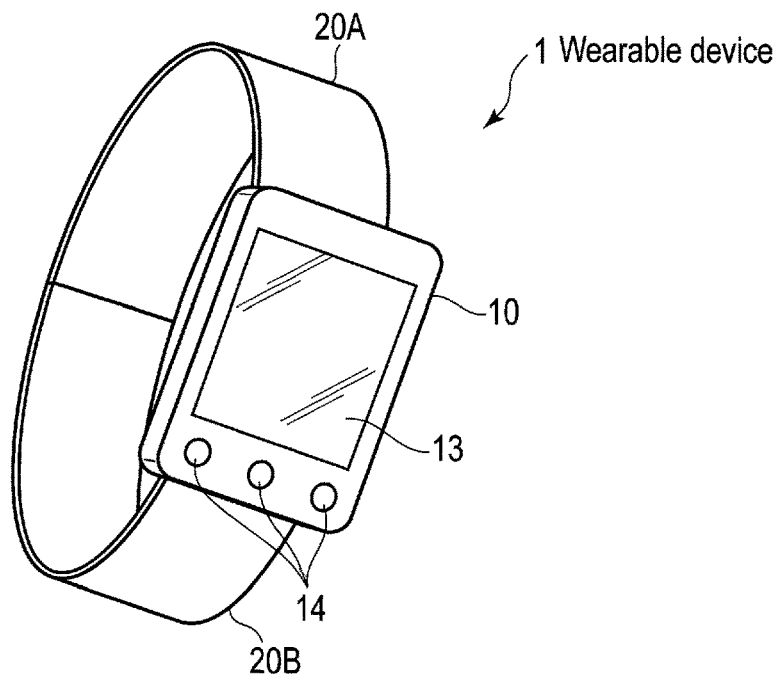
F I G. 1
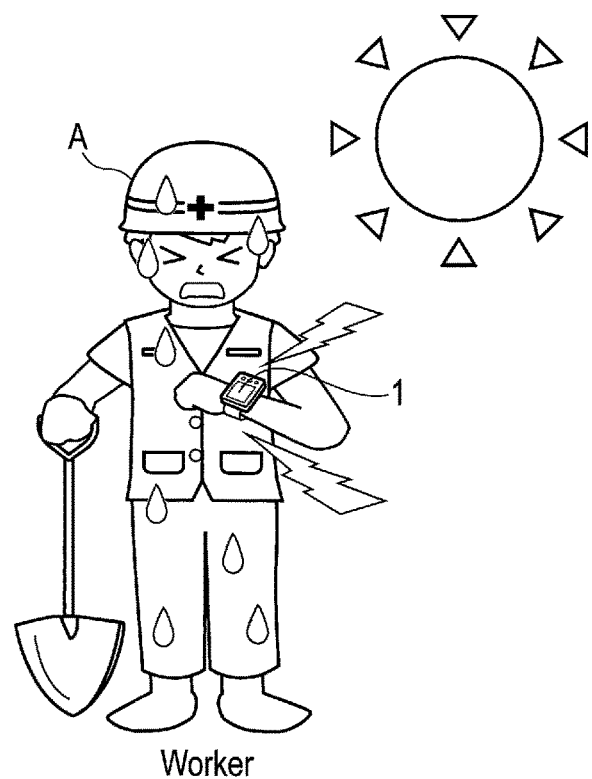
F I G. 2

ELECTRONIC DEVICE, SYSTEM, AND BODY CONDITION ESTIMATION METHOD

CROSS-REFERENCE TO RELATED APPLICATIONS

This application is based upon and claims the benefit of priority from Japanese Patent Application No. 2018-131606, filed Jul. 11, 2018, the entire contents of which are incorporated herein by reference.

FIELD

Embodiments described herein relate generally to an electronic device, a system, and a body condition estimation method.

BACKGROUND

In recent years, supervision has started to be carried out such that each worker does not have a heat stroke by making each worker wear an electronic device which is called a wearable device and the like and acquiring information on each worker working in a worksite in summer.

For example, adjustment of a reference value for detecting a sign of a heat stroke depending on a working environment has been generally performed. However, an adaptive estimation of a body condition of each worker in consideration of a period following restart of a work after taking a break in which heat or the like largely affects a change in body condition, has not been performed.

BRIEF DESCRIPTION OF THE DRAWINGS

FIG. 1 is a diagram showing an example of the exterior of a wearable device (electronic device) according to an embodiment.

FIG. 2 is a diagram showing an example in which the wearable device according to the embodiment is worn.

DETAILED DESCRIPTION

Figure 3:
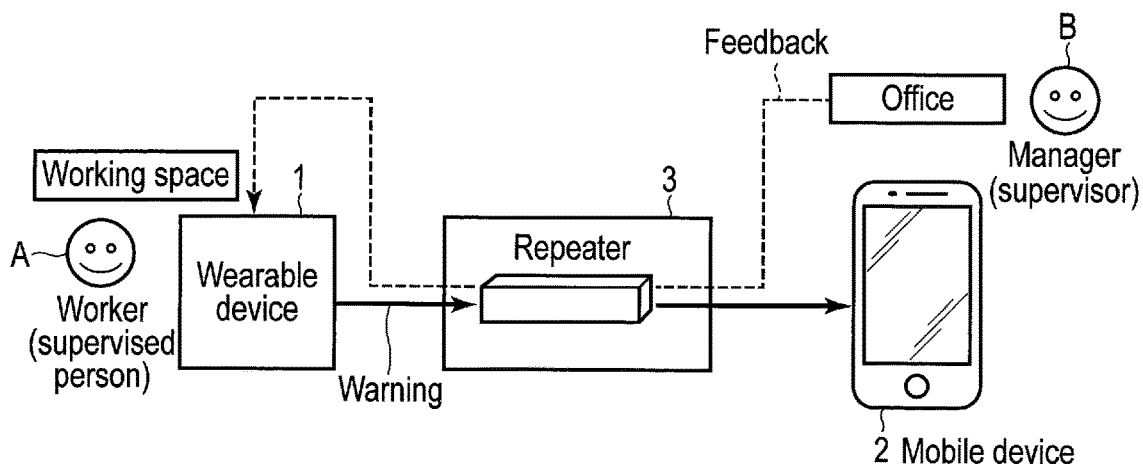
FIG. 3 is a diagram showing an example of a system configured by applying the wearable device according to the embodiment.

Various embodiments will be described hereinafter with reference to the accompanying drawings.

In general, according to one embodiment, an electronic device includes a biological information acquisition processor, a body condition estimation processor, and a motion change detector. The biological information acquisition processor is implemented by one or more hardware processors, and acquires biological information of a living body including information about the living body. The body condition estimation processor is implemented by one or more hardware processors, and estimates a body condition of the living body based at least in part on the biological information. The motion change detector is implemented by one or more hardware processors, and detects a motion change of the living body based at least in part on the biological information. The body condition estimation processor corrects a reference value used during body condition estimation or changes a body condition estimation method based at least in part on the motion change of the living body.

FIG. 1 is a diagram showing an example of the exterior of a wearable device (electronic device) 1 according to an embodiment. The wearable device 1 includes a main body 10, and bands 20A and 20B installed at an upper end and a lower end of the main body 10, respectively, and formed of a flexible material. A display 13 is disposed at a central portion of a front surface of the main body 10, and a group of switches 14 are disposed at a lower portion of the front surface of the main body 10, that is, in the vicinity of a lower side of the display 13. In addition, although not shown in FIG. 1, various sensors are disposed in a peripheral wall of the main body 10. The sensors will be described later with reference to FIG. 4. For example, a pulse sensor, a perspiration sensor, or the like is disposed on a back surface of the main body 10 in contact with a living body, and a temperature sensor, a humidity sensor, or the like is disposed near the switches 14 in the vicinity of the lower side of the display 13. In addition, an acceleration sensor or the like is also mounted inside the main body 10.

The wearable device 1 can be mounted on an arm portion of a supervised person such as a worker A by the bands 20A and 20B formed of a flexible material, in a state where the back surface of the main body 10 is in contact with a living body as shown in FIG. 2. Here, it is assumed that the wearable device 1 is implemented as a watch type. The wearable device 1 is not limited thereto, and can also be implemented as an eyeglass type having a portion in contact with a living body such as a pad, temples, or the like. Further, in the case where biological information can be acquired without being in contact with the living body, the wearable device 1 may not necessarily have a wearable form. Here, an electronic device used while being worn on the body is referred to as the wearable device 1 regardless of whether or not the electronic device is in contact with a living body, including the case where the electronic device is put into a pocket or is attached to clothes. In addition, here, it is assumed that a living body is a human. The living body is not limited thereto, and may also be a dog, a cat, livestock, or the like. That is, the wearable device 1 can also be applied to management of a body condition of an animal.

FIG. 3 is a diagram showing an example of a system configured by applying the wearable device 1. The system is a system for a manager B (supervisor) in a remote location, for example, an office to supervise a body condition of the worker A in order to prevent the body condition of the worker A working in a working space from becoming poor in advance. In this system, the wearable device 1 mounted on the worker A acquires biological information of the worker A and detects a sign of a poor body condition of the worker A based on the acquired biological information. Here, "body condition" means sweat, myalgia and nausea resulting from heat, Frostbitten, hypothermia, sleepiness and chill resulting from cold, depression, stomachache and palpitations resulting from stress and giddiness, headache and fever resulting from fatigue.

The wearable device 1 has a wireless communication function, and when detecting the sign of the poor body condition of the worker A, notifies a mobile device 2 such as a smartphone or the like carried by the manager B of a warning via a repeater 3. The repeater 3 includes, for example, an access point of a wireless local area network (LAN), or the like. When the wireless LAN is connected to the Internet, communication between the wearable device 1 and the mobile device 2 can be performed via the Internet. It should be noted that the communication between the wearable device 1 and the mobile device 2 may be directly performed without going through the repeater 3. In addition, a device used by the manager B to supervise the body condition of the worker A may be uncarriable, for example, may be a stationary personal computer which is called a desktop type, or the like.

The mobile device 2 receiving the warning notification from the wearable device 1 reports the fact that the sign of the poor body condition of the worker A is detected to the manager B. Various methods such as displaying a warning message, outputting a warning sound, or the like can be adopted for this report. The manager B, recognizing that the sign of the poor body condition of the worker A is detected, performs an instruction operation such as an advice to take a break, or the like on the mobile device 2, and the instruction is fed back to the wearable device 1 via the repeater 3. The wearable device 1 transfers the instruction to the worker A by displaying the instruction in, for example, the display 13. The worker A receiving the instruction, for example, takes a break, such that it is possible to prevent the body condition from becoming poor in advance.

Meanwhile, for example, in a worksite in summer, it is important to prepare a countermeasure for a heat stroke. Contrary to popular belief that stamina is recovered by taking a break, an influence of heat on the body condition tends to be greater in a period following restart of a work after taking a break, in comparison to that in a period before taking a break. For example, since tolerance to heat is decreased when being exposed to an air-conditioner while taking a break or stopping the work, the body condition is easily affected by heat right after taking a break. In addition to heat, stress arising from the work tends to be greater in the period following the restart of the work after taking a break. The wearable device 1 according to the present embodiment performs an adaptive estimation of a body condition in consideration of the period following restart of a work in which the body condition is easily changed, and hereinafter, this will be described in detail.

The biological information acquired by the wearable device 1 includes information about the living body, for example, motion information such as an amount of body motion or the like, environment information such as a temperature, a humidity, or the like, position information, and the like, in addition to information on a biological phenomenon such as a pulse rate, an amount of perspiration, or the like. Here, all information on the living body is referred to as biological information.

Figure 4:
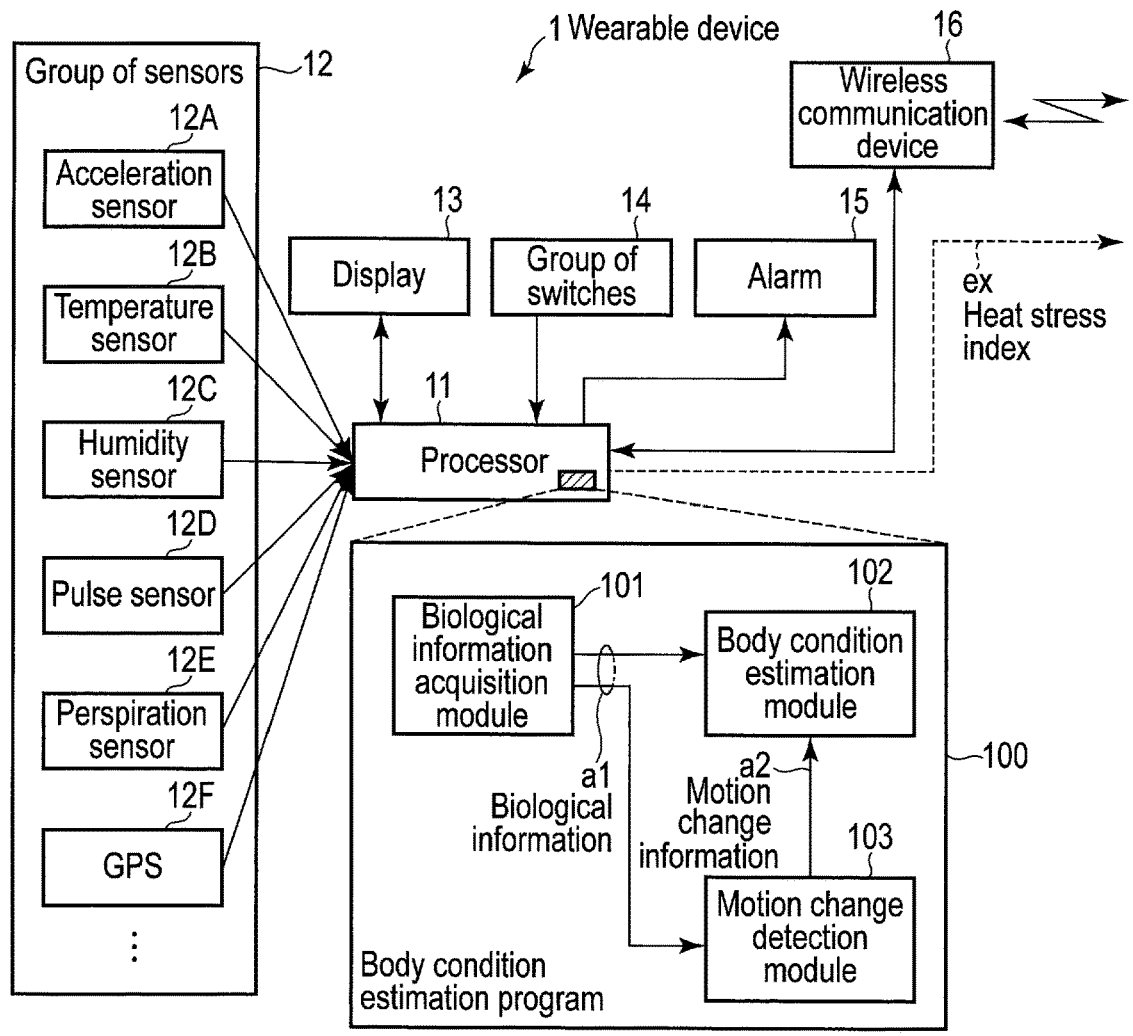
FIG. 4 is a diagram showing an example of a configuration of the wearable device according to the embodiment.

FIG. 4 is a diagram showing an example of a configuration of the wearable device 1.

As shown in FIG. 4, the wearable device 1 includes a processor 11, a group of sensors 12, an alarm 15, a wireless communication device 16, and the like in addition to the display 13 or the group of switches 14 described above.

The processor 11 is a device controlling each component in the wearable device 1. The processor 11 executes various programs for causing the wearable device 1 to perform a desired operation, the various programs being stored in an embedded storage. The various programs include a body condition estimation program 100 shown in FIG. 4, and the processor 11 executes the body condition estimation program 100 such that respective processors (processing modules) such as a biological information acquisition module 101, a body condition estimation module 102, and a motion change detection module 103 are built into the wearable device 1. Some or all of the respective processors (processing modules) such as the biological information acquisition module 101, the body condition estimation module 102, and the motion change detection module 103 may also be built as an integrated circuit (electronic circuit), or the like. In addition, the various programs further include a program for building a transfer module displaying the instruction fed back from the mobile device 2 described above in the display 13, or informing of a fact that the instruction is transferred, through the alarm 15. When informing the fact that the instruction is transferred, a vibrator may be used in place of the alarm 15, or both of the vibrator and the alarm 15 may be used.

The biological information acquisition module 101 acquires a sensor value of the group of sensors 12 as the biological information. The group of sensors 12 includes an acceleration sensor 12A, a temperature sensor 12B, a humidity sensor 12C, a pulse sensor 12D, a perspiration sensor 12E, a global positioning system (GPS) 12F, and the like. The biological information acquired by the biological information acquisition module 101 is supplied to the body condition estimation module 102 and the motion change detection module 103 (a1 in FIG. 4).

The body condition estimation module 102 estimates the body condition of the living body by using the biological information received from the biological information acquisition module 101, and detects the sign of the poor body condition. The body condition estimation module 102 estimates, for example, a heat stroke-heat stress index. The heat stroke-heat stress index, which is a value indicating a risk of causing a heat stroke, can be calculated from, for example, a wet bulb globe temperature (WBGT) and a metabolic rate of the living body. The WBGT and the metabolic rate of the living body can be calculated from the biological information including the motion information and the environment information which is acquired by the group of sensors 12. When the heat stroke-heat stress index is calculated, the body condition estimation module 102 determines whether or not the calculated value exceeds a reference value (threshold value) which is set for detecting the sign of the heat stroke. When the calculated value exceeds the reference value, the body condition estimation module 102 notifies the mobile device 2 of the warning through the wireless communication device 16 performing the wireless communication function described above. In this notification, a ground for detecting the sign of the poor body condition, for example, the heat stroke-heat stress index or the like is attached.

Similarly, the body condition estimation module 102 can also calculate a frostbite-cold stress index, a momentary-chronic stress index, a depression risk index, a fatigue index, and the like from the biological information including the motion information and the environment information acquired by the group of sensors 12. When the calculated value exceeds a reference value for detecting the sign of the poor body condition, the body condition estimation module 102 notifies the mobile device 2 of the warning. A method of calculating each index is not limited to a certain method, but various methods known in the art can be applied.

For example, a method is known in which a stress index (LF/HF: sympathetic nerve activity) is calculated from a high-frequency fluctuation component (HF) and a low-frequency component (LF) appearing in variation in a heartbeat. In the method, a value obtained by dividing the LF component by the HF component is used as the stress index based on a fact that the HF component is decreased and the LF component is larger than the HF component in a stress state in which a sympathetic nerve is predominant. The variation in the heartbeat can be calculated from the biological information (pulse) acquired by the group of sensors 12 (pulse sensor 12D). A method of calculating the heat stroke-heat stress index is also not limited to the method in which the heat stroke-heat stress index is calculated from the WBGT and the metabolic rate of the living body, but other methods known in the art may be applied.

Meanwhile, the motion change detection module 103 receiving the biological information from the biological information acquisition module 101 in parallel with the body condition estimation module 102 detects a motion change of the living body from the biological information. Specifically, the motion change detection module 103 detects that a state of the worker A shifts from a working state (first state) to a break state (second state), or the state of the worker A shifts from the break state to the working state.

The motion change detection module 103 determines whether or not an amount of body motion of the living body exceeds a reference value (threshold value) set for detecting a low activity state. The motion change detection module 103 determines that the living body is in a non-low activity state when the amount of body motion of the living body exceeds the reference value. Whereas, the motion change detection module 103 determines that the living body is in the low activity state when the amount of body motion of the living body is equal to or less than the reference value. Here, the non-low activity state means the working state, and the low activity state means the break state. The motion change detection module 103 detects that the motion of the living body is changed from the working state to the break state, or the motion of the living body is changed from the break state to the working state based on the determination result. At this time, the motion change detection module 103 detects, for example, the change from the break state to the working state in the case where the determination that the amount of body motion of the living body exceeds the reference value is continuously made. By doing so, a situation where the motion change detection module 103 erroneously detects that the state of the living body is changed to the working state when the amount of body motion of the living body momentarily exceeds the reference value while taking a break is prevented.

When detecting shifting from the break state to the working state, the motion change detection module 103 supplies motion change information to the body condition estimation module 102 (a2 in FIG. 4). The motion change information is information for correcting a reference value which is used by the body condition estimation module 102 to detect the sign of the poor body condition, or for returning the corrected reference value to the reference value before the correction. In more detail, when detecting the shifting from the break state to the working state, the motion change detection module 103 supplies motion change information for adjusting the reference value to be smaller to the body condition estimation module 102. Then, after a predetermined time elapses, the motion change detection module 103 supplies motion change information for causing the body condition estimation module 102 to return the adjusted reference value to the value before the adjustment. By the operation of the motion change detection module 103 described above, it is easy for the body condition estimation module 102 to detect the sign of the poor body condition in a time zone in which the body condition is easily affected, which is the period following the restart of the work after taking a break.

It should be noted that the body condition estimation module 102 may autonomously perform the process of returning the adjusted reference value to the value before the adjustment after a predetermined period elapses, regardless of the supply of the motion change information from the motion change detection module 103. In more detail, when receiving the motion change information from the motion change detection module 103, the body condition estimation module 102 may correct the reference value and return the corrected reference value to the value before the correction after the predetermined period elapses.

In addition, as described above, as the method of calculating each index related to the body condition, various methods known in the art can be applied. Therefore, the method itself may be changed instead of correcting a reference value of any one method. In more detail, the method may be changed to a method in which it is easy to detect the sign of the poor body condition, in a predetermined period following the restart of the work after taking a break. For example, only in the predetermined period, a method causing a large processing amount and large power consumption, but being capable of precisely estimating the body condition, may be applied.

An example in which the wearable device 1 according to the present embodiment detects the sign of the poor body condition will be described with reference to FIG. 5.

Figure 5:
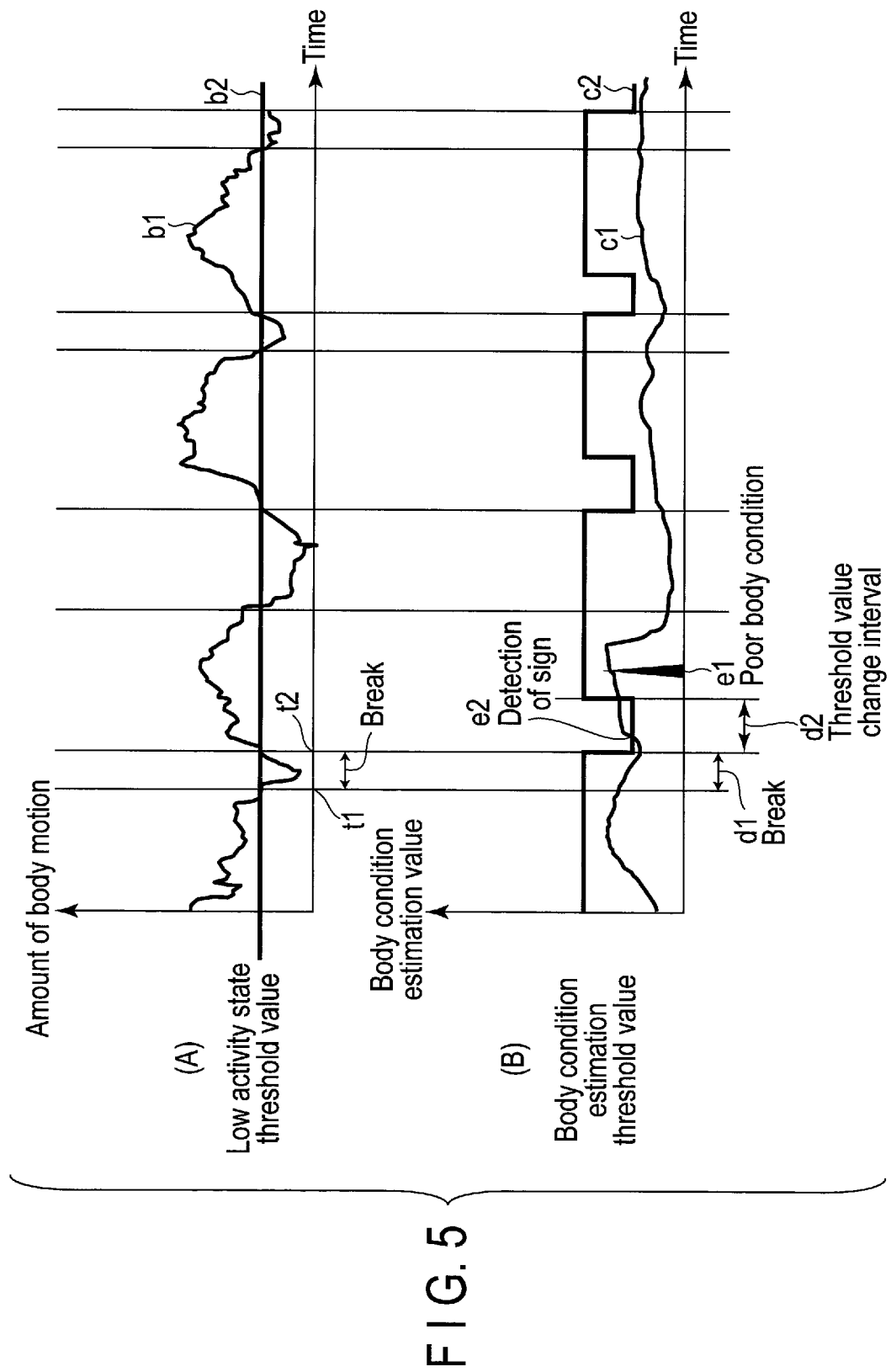
FIG. 5 is a diagram for describing an example in which the wearable device according to the embodiment detects a sign of a poor body condition.

In FIG. 5, (A) is a graph showing detection of a motion change by the motion change detection module 103, and (B) is a graph showing detection of the sign of the poor body condition by the body condition estimation module 102. Horizontal axes in (A) and (B) of FIG. 5 both represent time identically. Further, a vertical axis in (A) of FIG. 5 represents an amount of body motion, and a vertical axis in (B) of FIG. 5 represents a body condition estimation value. The body condition estimation value is, for example, the heat stroke-heat stress index or the like.

In (A) of FIG. 5, a line segment indicated by reference numeral b1 represents a time-series change of the amount of body motion of the living body. Further, in (A) of FIG. 5, a line segment indicated by reference numeral b2 represents a low activity state threshold value set for determining whether or not the living body is in the low activity state. The motion change detection module 103 determines that the living body is in the non-low activity state, that is, the working state, when the amount of body motion of the living body exceeds the low activity state threshold value. Whereas, the motion change detection module 103 determines that the living body is in the low activity state, that is, the break state, when the amount of body motion of the living body is equal to or less than the low activity state threshold value. The motion change detection module 103 detects that the motion of the living body is changed from the working state to the break state (t1), or the motion of the living body is changed from the break state to the working state (t2) based on the determination result. When detecting that the motion of the living body is changed from the break state to the working state, the motion change detection module 103 supplies the motion change information to the body condition estimation module 102.

Meanwhile, in (B) of FIG. 5, a line segment indicated by reference numeral c1 represents a time-series change of the body condition estimation value. Further, in (B) of FIG. 5, a line segment indicated by reference numeral c2 represents a body condition estimation threshold value set for detecting the sign of the poor body condition. When the calculated body condition estimation value exceeds the body condition estimation threshold value, the body condition estimation module 102 determines that the sign of the poor body condition is shown. That is, the sign of the poor body condition is detected.

In addition, the body condition estimation module 102 corrects the body condition estimation threshold value when receiving the motion change information from the motion change detection module 103. In more detail, the body condition estimation module 102 adjusts the body condition estimation threshold value to be smaller so that the sign of the poor body condition is easily detected. The corrected body condition estimation threshold value is maintained for a predetermined period. The returning to an original value after the predetermined period elapses may be performed based on the motion change information from the motion change detection module 103 or may be autonomously performed by the body condition estimation module 102 as described above.

As a result, a threshold value change interval d2 in which the body condition estimation threshold value is adjusted to be smaller for a predetermined period is provided in the period following the restart of the work after taking a break d1. It is preferable that this threshold value change interval is longer than, for example, a time taken for the living body to adapt to a working environment. As a method of calculating the time, various methods known in the art, such as a statistical method, can be applied.

Here, a case is assumed where the threshold value change interval is not provided. Further, a case is assumed where the body condition of the living body is poor at a point in time indicated by reference numeral e1. In this case, the body condition estimation value calculated by the body condition estimation module 102 does not exceed the body condition estimation threshold value until the point in time indicated by the reference numeral e1. Therefore, even when the sign of the poor body condition is shown in the time zone in which the body condition is easily affected, which is the period following the restart of the work after taking a break, the sign of the poor body condition is overlooked. The time zone in which the body condition is easily affected, which is the period following the restart of the work after taking a break, is a time zone in which the body condition estimation value when the sign of the poor body condition is shown tends to be smaller, in comparison to that in other time zones.

In contrast, in the wearable device 1 of the present embodiment in which the threshold value change interval is provided in which the body condition estimation threshold value is adjusted to be smaller for a predetermined period, the body condition estimation value calculated by the body condition estimation module 102 exceeds the body condition estimation threshold value at a point in time indicated by reference numeral e2, and therefore, the sign of the poor body condition can be detected without being overlooked.

Correction in the threshold value change interval of the body condition estimation threshold value may be performed only when a preset condition is satisfied. For example, in the case where it is estimated that the living body at the time of detection of the low activity state is located outdoors, when the non-low activity state is detected later, the motion change detection module 103 may supply motion change information for changing the body condition estimation threshold value to the body condition estimation module 102. In addition, in the case where a period in which the low activity state is detected exceeds a preset period, or an average value of amounts of body motion of the living body in a corresponding period is equal to or less than a preset value, when the non-low activity state is detected later, the motion change detection module 103 may stop supplying the motion change information for changing the body condition estimation threshold value to the body condition estimation module 102. That is, the body condition estimation threshold value may not be corrected.

Alternatively, a reference for determination of whether or not the body condition estimation threshold value needs to be corrected may be decided by accumulating and analyzing a result of past body condition estimation or biological information acquired in the past. Alternatively, only in a case where the stress index (LF/HF: sympathetic nerve activity) described above is equal to or more than a preset value, the body condition estimation module 102 may correct the body condition estimation threshold value when receiving the motion change information from the motion change detection module 103. In other words, in a case where the stress index is smaller than the preset value, the body condition estimation module 102 may not correct the body condition estimation threshold value even when receiving the motion change information from the motion change detection module 103.

Alternatively, for example, when the motion change detection module 103 monitors perspiration in the period in which the low activity state is detected, and the perspiration is continued until the non-low activity state is detected, the motion change information for changing the body condition estimation threshold value may be supplied to the body condition estimation module 102.

Alternatively, a correction range of the body condition estimation threshold value may be controlled in addition to controlling whether or not to correct the body condition estimation threshold value. For example, the correction range of the body condition estimation threshold value may be determined depending on a value of the stress index as described above, or the like. Alternatively, for example, a body mass index (BMI) of the living body is input in advance or at the time of mounting the wearable device 1, and the correction range of the body condition estimation threshold value may be determined depending on the BMI.

When the sign of the poor body condition is detected, the mobile device 2 is notified of a warning, and, for example, an instruction operation such as an advice to take a break, or the like is performed by the mobile device 2. The instruction is fed back to the wearable device 1 and transferred to the living body. By doing so, it is possible to prevent the body condition of the living body from becoming poor in advance.

Figure 6:
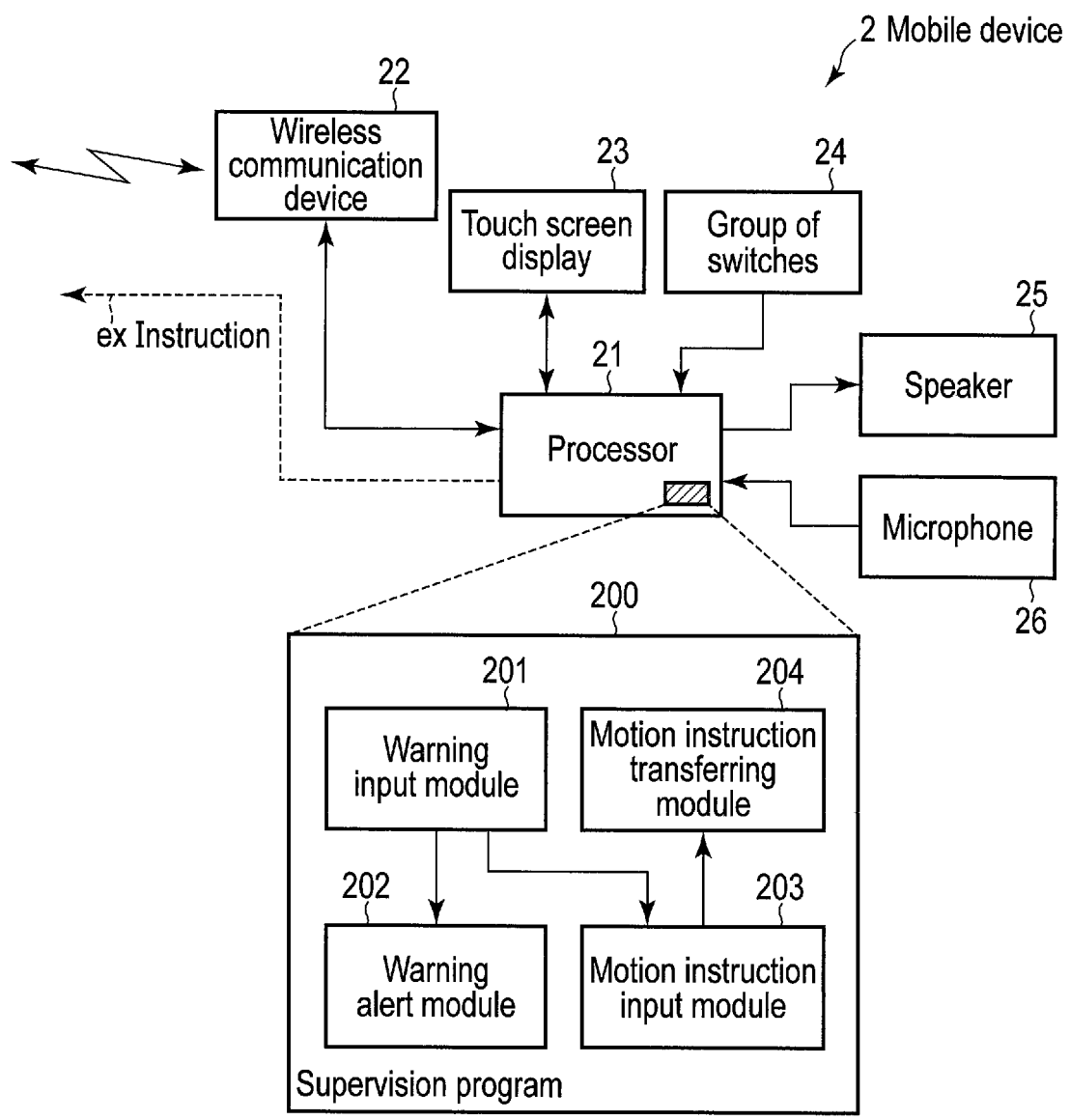
FIG. 6 is a diagram showing an example of a configuration of a mobile device configuring the system in cooperation with the wearable device according to the embodiment.

FIG. 6 is a diagram showing an example of a configuration of the mobile device 2.

As shown in FIG. 6, the mobile device 2 includes a processor 21, a wireless communication device 22, a touch screen display 23, a group of switches 24, a speaker 25, a microphone 26, and the like.

The processor 21 is a device controlling each component in the mobile device 2. The processor 21 executes various programs for causing the mobile device 2 to perform a desired operation, the various programs being stored in an embedded storage. The various programs include a supervision program 200 shown in FIG. 6, and the processor 21 executes the supervision program 200 such that respective processors (processing modules) such as a warning input module 201, a warning alert module 202, a motion instruction input module 203, and a motion instruction transferring module 204 are built into the mobile device 2. Some or all of the respective processors (processing modules) such as the warning input module 201, the warning alert module 202, the motion instruction input module 203, and the motion instruction transferring module 204 may also be built as an integrated circuit (electronic circuit), or the like. In addition, the various programs also include a program for informing of an incoming call through the touch screen display 23 or the speaker 25, starting or ending a call by a touch operation on the touch screen display 23, or inputting or outputting a voice for a call through the microphone 26 or the speaker 25.

The warning input module 201 inputs a warning notification received from the wearable device 1 through the wireless communication device 22. When the warning notification from the wearable device 1 is input, the warning input module 201 notifies the warning alert module 202 and the motion instruction input module 203 of the input. When receiving the notification from the warning input module 201, the warning alert module 202 performs a report through, for example, the touch screen display 23 or the speaker 25 in order to inform the manager B of a fact that the sign of the poor body condition of the worker A on whom the wearable device 1 is mounted is detected. At the time of the report, it is preferable that a ground for detecting the sign of the poor body condition that is included in the warning notification from the wearable device 1, for example, the heat stroke-heat stress index or the like is indicated.

In the motion instruction input module 203, the manager B inputs an instruction for the worker A in response to the report from the warning alert module 202. The input of the instruction may be performed by, for example, inputting a character through a touch operation on the touch screen display 23, or selecting any one of options prepared in advance. For example, when receiving the notification from the warning input module 201, the motion instruction input module 203 displays a screen for inputting the instruction on the touch screen display 23. When a ground for detecting the sign of the poor body condition, for example, the heat stroke-heat stress index or the like is indicated, it is possible to input an appropriate instruction in response to the value. The motion instruction transferring module 204 transfers the instruction input through the motion instruction input module 203 to the wearable device 1 through the wireless communication device 22.

When detecting the sign of the poor body condition, the wearable device 1 may issue a warning to the living body through, for example, the alarm 15. That is, the wearable device 1 may be implemented as an electronic device operating under a standalone environment and preventing a body condition of a user from becoming poor in advance.

Figure 7:
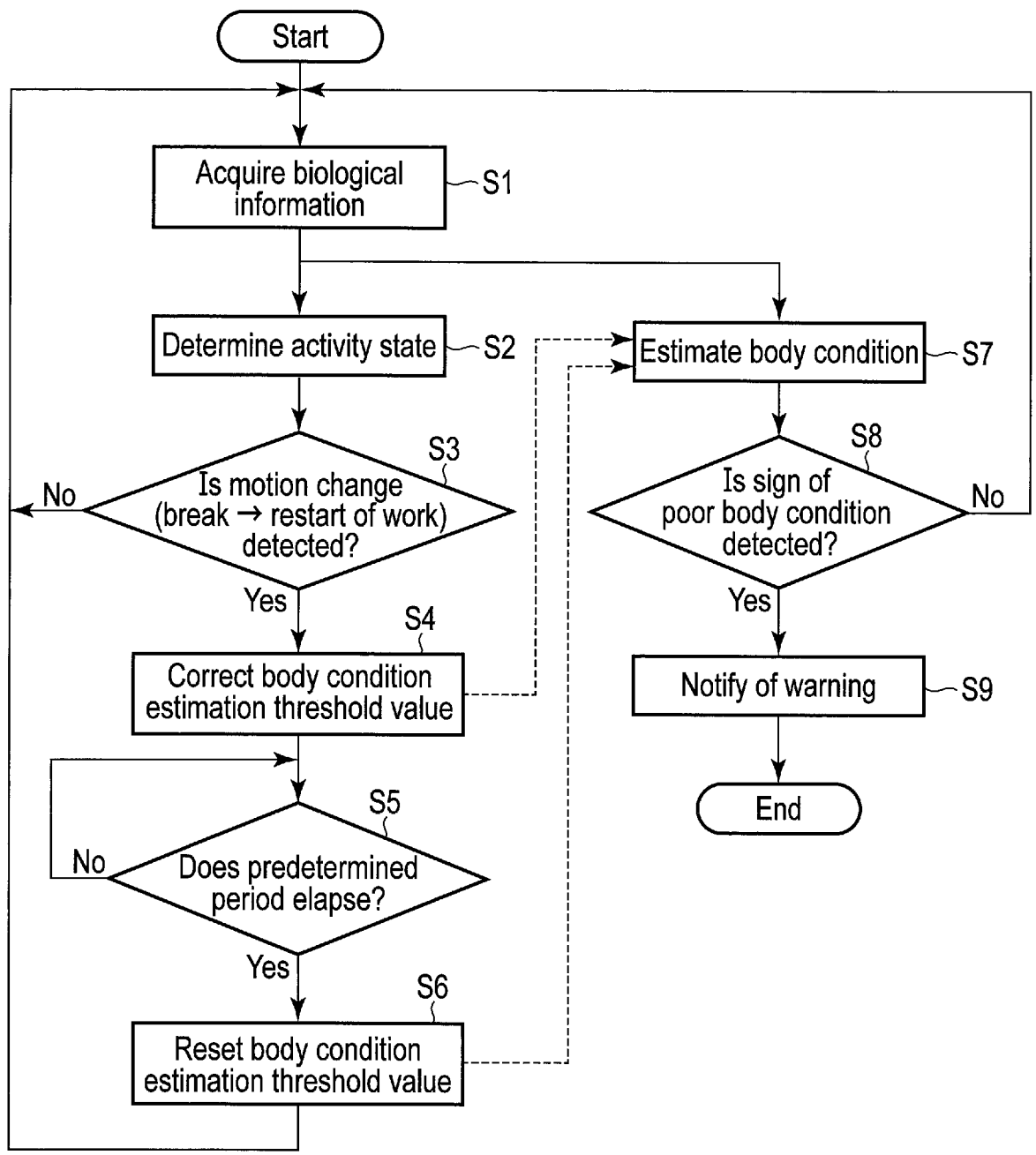
FIG. 7 is a flowchart showing an order of operations of the wearable device according to the embodiment.

FIG. 7 is a flowchart showing an order of operations of the wearable device 1.

The wearable device 1 acquires biological information (step S1). The wearable device 1 determines an activity state by using the acquired biological information (step S2). The wearable device 1 determines whether or not a motion change of the living body from the break state to the working state is detected based on the determination result (step S3). When the motion change of the living body is detected (step S3: YES), the wearable device 1 corrects the body condition estimation threshold value for detecting the sign of the poor body condition (step S4). In more detail, the body condition estimation threshold value is adjusted to be smaller so that the sign of the poor body condition is easily detected.

When the body condition estimation threshold value is corrected, the wearable device 1 checks whether or not a predetermined time elapses from the correction (step S5). When the predetermined time elapses (step S5: YES), the wearable device 1 returns the corrected body condition estimation threshold value to the value before correction (step S6).

Further, the wearable device 1 performs steps S7 to S9 in parallel with steps S2 to S6. The wearable device 1 estimates the body condition of the living body by using the acquired biological information (step S7), and determines whether or not the sign of the poor body condition is detected (step S8). When the sign of the poor body condition is detected (step S8: YES), the wearable device 1 notifies the mobile device 2 of a warning (step S9).

As described above, the wearable device 1 can perform an adaptive estimation of a body condition in consideration of a period following restart of a work in which the body condition is easily changed.

Figure 8:
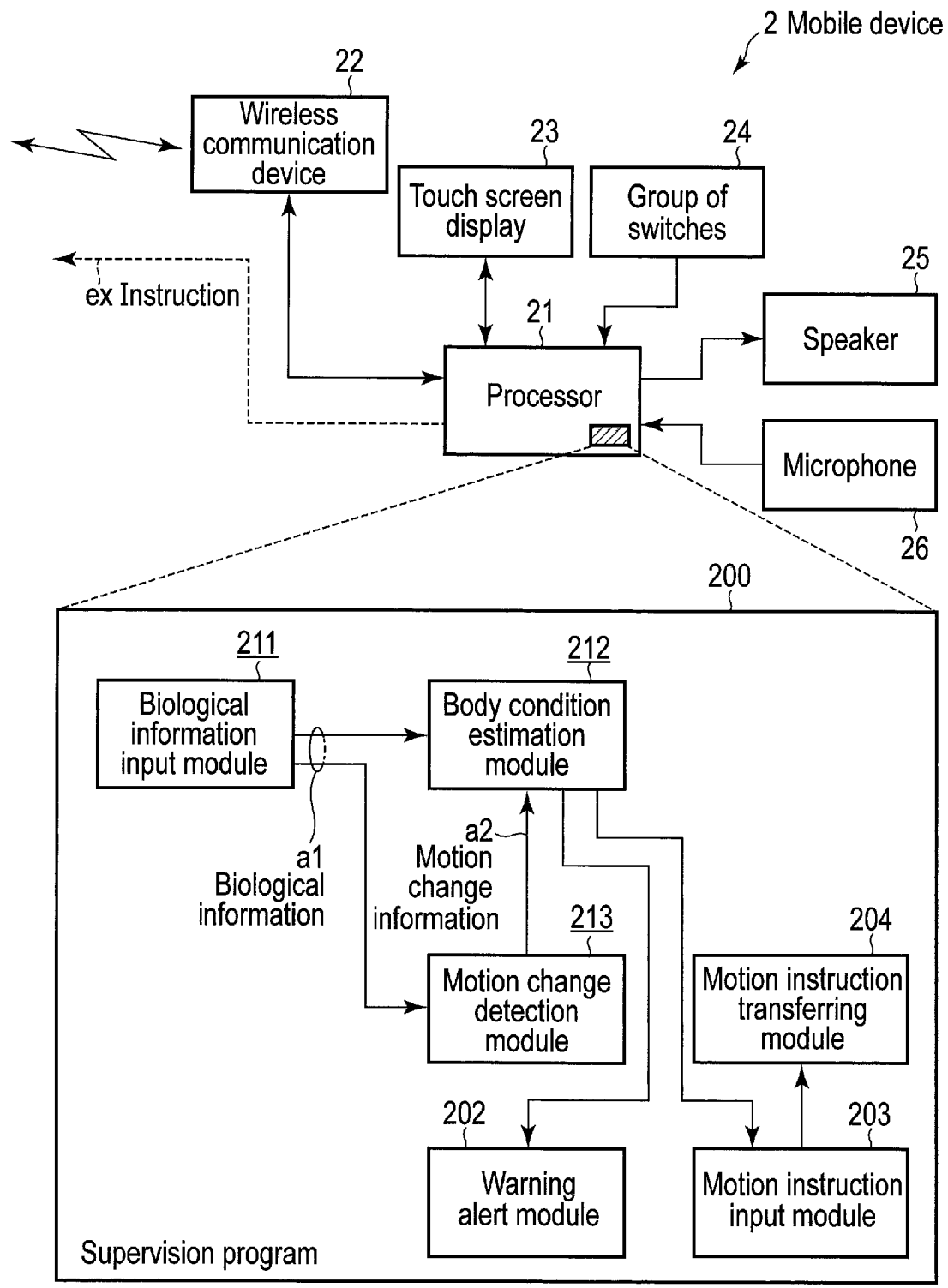
FIG. 8 is a diagram showing an example of another configuration of the mobile device configuring the system in cooperation with the wearable device according to the embodiment.

Meanwhile, the adaptive estimation of a body condition in consideration of a period following restart of a work in which the body condition is easily changed may be performed by the mobile device 2. That is, the wearable device 1 only serves to acquire the biological information and transfer the acquired biological information to the mobile device 2, or transfer the instruction from the mobile device 2 to the living body, the estimation of the body condition for detecting the sign of the poor body condition, or the detection of the motion change for correcting the body condition estimation threshold value may be performed by the mobile device 2 by using the biological information transferred from the wearable device 1. FIG. 8 shows an example of a configuration of the mobile device 2 in this case.

As shown in FIG. 8, in the mobile device 2 in this case, the processor 11 executes the supervision program 200, such that respective processors (processing modules) such as a biological information input module 211, a body condition estimation module 212, and a motion change detection module 213 are built into the mobile device 2, instead of the warning input module 201 described above.

In the biological information input module 211, biological information received from the wearable device 1 through the wireless communication device 22 is input. The biological information input module 211 supplies the input biological information to the body condition estimation module 212 and the motion change detection module 213.

The body condition estimation module 212 and the motion change detection module 213 correspond to the body condition estimation module 102 and the motion change detection module 103 described above, respectively. The body condition estimation module 212 estimates the body condition of the living body by using the biological information received from the biological information input module 211 and detects the sign of the poor body condition, and the motion change detection module 213 detects the motion change of the living body by using the biological information received from the biological information input module 211.

When the sign of the poor body condition is detected, the body condition estimation module 212 notifies the warning alert module 202 and the motion instruction input module 203 of the detection. In addition, when the motion change of the living body is detected, the motion change detection module 213 corrects the body condition estimation threshold value by supplying the motion change information to the body condition estimation module 212.

Also in this case, the threshold value change interval in which the body condition estimation threshold value is adjusted to be smaller for a predetermined period can be provided in the period following the restart of the work after taking a break. As a result, an adaptive estimation of a body condition in consideration of a period following restart of a work in which the body condition is easily changed can be performed.

In the above description, the example has been described in which whether or not the state of the living body is the low activity state, that is, whether the state of the living body is the break state or the working state is determined based on the amount of body motion of the living body. The present invention is not limited thereto. For example, whether the state of the living body is the break state or the working state may be determined based on location information of the living body. For example, in a case of a work that an amount of body motion is relatively small in a working space under a severe environment such as an inventory check in a refrigerated storage, whether the state of the living body is the break state or the working state is determined based on the location information of the living body, which is effective.

In addition, in the above description, the example is described in which the body condition estimation threshold value is adjusted to be smaller in the threshold value change interval provided in the period following the restart of the work after taking a break. The body condition estimation threshold value may also be adjusted to be larger depending on an index calculated by the body condition estimation module 102. For example, when there is an index which tends to be erroneously detected in the period following the restart of the work after taking a break, conversely, the body condition estimation threshold value may be adjusted to be larger for a predetermined period following the restart of the work after taking a break, for the index.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An electronic device comprising:
a biological information acquisition processor implemented by one or more hardware processors that acquires biological information of a living body comprising information about the living body;
a body condition estimation processor implemented by one or more hardware processors that estimates a body condition of the living body based at least in part on the biological information; and
a motion change detector implemented by one or more hardware processors that detects a motion change of the living body based at least in part on the biological information,
wherein the body condition estimation processor corrects a reference value of body condition estimation or changes a body condition estimation method based at least in part on the motion change of the living body, and returns the corrected reference value of the body condition estimation to the reference value before the correction or returns the changed body condition estimation method to the method before the change after a first period elapses from the correction of the reference value of the body condition estimation or the change of the body condition estimation method.

2. The electronic device of claim 1, wherein the motion change detector detects the motion change of the living body based at least in part on an amount of body motion of the living body included in the biological information.

3. The electronic device of claim 2, wherein:
the motion change detector further detects that the motion change of the living body from a first state to a second state or from the second state to the first state occurs; and
the body condition estimation processor corrects the reference value used during the body condition estimation or changes the body condition estimation method, when a change from the second state to the first state is detected.

4. The electronic device of claim 3, wherein:
the first state comprises a non-low activity state in which the amount of body motion of the living body exceeds a threshold value; and
the second state comprises a low activity state in which the amount of body motion of the living body is equal to or less than the threshold value.

5. The electronic device of claim 3, wherein the biological information acquisition processor acquires state information comprising at least one of a pulse rate or an amount of perspiration of the living body as the biological information, and acquires motion information comprising the amount of body motion of the living body and at least one of environment information comprising at least one of a temperature or a humidity around the living body, or location information of the living body, as the information about the living body.

6. The electronic device of claim 3, wherein the body condition estimation processor estimates one or more of a stroke-heat stress index, a frostbite-cold stress index, a momentary-chronic stress index, a depression risk index, or a fatigue index.

7. The electronic device of claim 1, wherein:
the motion change detector further detects that the motion change of the living body from a first state to a second state or from the second state to the first state occurs; and
the body condition estimation processor corrects the reference value used during the body condition estimation or changes the body condition estimation method, when a change from the second state to the first state is detected.

8. The electronic device of claim 1, wherein the biological information acquisition processor acquires state information comprising at least one of a pulse rate or an amount of perspiration of the living body as the biological information, and acquires motion information comprising the amount of body motion of the living body and at least one of environment information comprising at least one of a temperature or a humidity around the living body, or location information of the living body, as the information about the living body.

9. An electronic device comprising:
a biological information acquisition processor implemented by one or more hardware processors that acquires biological information of a living body comprising information about the living body;

a body condition estimation processor implemented by one or more hardware processors that estimates one or more of a stroke-heat stress index, a frostbite-cold stress index, a momentary-chronic stress index, a depression risk index, or a fatigue index; and a motion change detector implemented by one or more hardware processors that detects a motion change of the living body based at least in part on the biological information, wherein the body condition estimation processor corrects a reference value of estimation of the one or more of the stroke-heat stress index, the frostbite-cold stress index, the momentary-chronic stress index, the depression risk index or the fatigue index, or changes a method of estimation of the one or more of the stroke-heat stress index, the frostbite-cold stress index, the momentary-chronic stress index, the depression risk index or the fatigue index, based at least in part on the motion change of the living body.

10. A system comprising:

a first device which is mounted on a supervised person; and a second device which is wirelessly connected to the first device and configured to be used to supervise a body condition of the supervised person, wherein the first device comprises:
  a biological information acquisition processor implemented by one or more hardware processors that acquires biological information of the supervised person comprising information about a living body,
  a body condition estimation processor implemented by one or more hardware processors that estimates the body condition of the supervised person based at least in part on the biological information, and notifies the second device of a warning related to the supervised person when a sign of a poor body condition of the supervised person is detected,
  a motion change detector implemented by one or more hardware processors that detects a motion change of the supervised person based at least in part on the biological information, and
  a transfer processor implemented by one or more hardware processors that transfers an instruction from a supervisor supervising the body condition of the supervised person to the supervised person, the instruction being transferred from the second device to the first device configured to notify the warning, the second device comprises:
  a report processor implemented by one or more hardware processors that reports the detection of the sign of the poor body condition of the supervised person to the supervisor when the warning notification is made, and
  an instruction transferring processor implemented by one or more hardware processors that transfers the instruction made by the supervisor in response to the reporting of the detection of the sign of the poor body condition of the supervised person for the supervised person to the first device, and the body condition estimation processor corrects a reference value used during body condition estimation or changes a body condition estimation method based at least in part on the motion change of the living body, and returns the corrected reference value of the body condition estimation to the reference value before the correction or returns the changed body condition estimation method to the method before the change after a first period elapses from the correction of the reference value of the body condition estimation or the change of the body condition estimation method.

11. A system comprising:

a first device which is mounted on a supervised person; and a second device which is wirelessly connected to the first device and used to supervise a body condition of the supervised person, wherein the first device comprises:
  a biological information acquisition processor implemented by one or more hardware processors that acquires biological information of the supervised person comprising information about a living body and transfers the acquired biological information to the second device, and
  a transfer processor implemented by one or more hardware processors that transfers an instruction from a supervisor supervising the body condition of the supervised person to the supervised person, the instruction being transferred from the second device to the first device, the second device comprises:
  a body condition estimation processor implemented by one or more hardware processors that estimates the body condition of the supervised person based at least in part on the biological information transferred from the first device,
  a motion change detector implemented by one or more hardware processors that detects a motion change of the supervised person based at least in part on the biological information transferred from the first device,
  a report processor implemented by one or more hardware processors that reports a warning related to the supervised person to the supervisor when a sign of a poor body condition of the supervised person is detected, and
  an instruction transferring processor implemented by one or more hardware processors that transfers the instruction made by the supervisor in response to the report reporting of the warning related to the supervised person for the supervised person to the first device, the body condition estimation processor corrects a reference value used during body condition estimation or changes a body condition estimation method based at least in part on the motion change of the living body, and returns the corrected reference value of the body condition estimation to the reference value before the correction or returns the changed body condition estimation method to the method before the change after a first period elapses from the correction of the reference value of the body condition estimation or the change of the body condition estimation method.

12. A body condition estimation method performed by an electronic device mounted on a living body, the body condition estimation method comprising:

acquiring biological information comprising an amount of body motion;

estimating a body condition of the living body based at least in part on the biological information;

detecting a motion change of the living body based at least in part on the biological information; and correcting a reference value of body condition estimation or changing the body condition estimation method based at least in part on the motion change of the living body, and returning the corrected reference value of the body condition estimation to the reference value before the correction or returning the changed body condition estimation method to the method before the change after a first period elapses from the correction of the reference value of the body condition estimation or the change of the body condition estimation method.

\* \* \* \* \*